US011433209B2

(12) United States Patent
Geraci et al.

(10) Patent No.: US 11,433,209 B2
(45) Date of Patent: Sep. 6, 2022

(54) MODULAR EXHALATION DEVICE THAT TRANSITIONS CIRCUITS BETWEEN ACTIVE AND NON-INVASIVE VENTILATION MODES

(71) Applicant: KONINKLIJKE PHILIPS N.V., Eindhoven (NL)

(72) Inventors: Antonio George Geraci, Monroeville, PA (US); Katelyn Jean Stavinga, Monroeville, PA (US); Elizabeth Hurley, Carlsbad, CA (US); Kevin Shick, Claridge, PA (US)

(73) Assignee: Koninklijke Philips N.V., Eindhoven (NL)

( * ) Notice: Subject to any disclaimer, the term of this patent is extended or adjusted under 35 U.S.C. 154(b) by 406 days.

(21) Appl. No.: 16/691,649

(22) Filed: Nov. 22, 2019

(65) Prior Publication Data
US 2020/0164171 A1   May 28, 2020

Related U.S. Application Data

(60) Provisional application No. 62/771,646, filed on Nov. 27, 2018.

(51) Int. Cl.
*A61M 16/08* (2006.01)
*A61M 16/10* (2006.01)
(Continued)

(52) U.S. Cl.
CPC .... *A61M 16/0833* (2014.02); *A61M 16/0816* (2013.01); *A61M 16/1065* (2014.02);
(Continued)

(58) Field of Classification Search
CPC .............. A61M 16/00; A61M 16/0003; A61M 16/0057; A61M 16/0066; A61M 16/08; A61M 16/0816; A61M 16/0833; A61M 16/0866; A61M 16/0875; A61M 16/1065; A61M 16/20; A61M 16/205; A61M 16/206; A61M 16/208
See application file for complete search history.

(56) References Cited

U.S. PATENT DOCUMENTS 7,617,824 B2   11/2009  Doyle
8,677,999 B2    3/2014  Cipollone et al.
(Continued)

*Primary Examiner* — Joseph D. Boecker
(74) *Attorney, Agent, or Firm* — Daniel H. Brean

(57) ABSTRACT

An exhalation device for a non-invasive ventilator, configured to reversibly convert between a passive ventilation configuration and an active ventilation configuration, comprising: (i) a housing with a first end and a second end, the housing defining a gas flow path extending between the first end and the second end; (ii) an exhalation port configured to passively release gas to the environment; (iii) an internal diaphragm positioned at an interface between the exhalation port and the housing, configured to allow release of gas exhalation; and (iv) an adapter comprising an adapter exhalation port and configured to reversibly engage the exhalation port to define a controlled exhalation flow path from the exhalation port to the adapter exhalation port, and comprising an internal air flow control configured to actively control the flow of exhalant through the controlled exhalation flow path.

16 Claims, 5 Drawing Sheets

(51) Int. Cl.
*A61M 16/20* (2006.01)
*A61M 16/00* (2006.01)

(52) U.S. Cl.
CPC ........ *A61M 16/206* (2014.02); *A61M 16/208* (2013.01); *A61M 16/0057* (2013.01); *A61M 16/0066* (2013.01)

(56) References Cited

U.S. PATENT DOCUMENTS

| | | |
|---|---|---|
| 8,800,560 B2 | 8/2014 | Alfieri et al. |
| 10,195,378 B2 | 2/2019 | Cyprowski et al. |
| 2011/0197884 A1 | 8/2011 | Duff et al. |
| 2014/0109907 A1* | 4/2014 | Doshi ................ A61M 16/208 128/204.21 |
| 2017/0014594 A1 | 1/2017 | Cole |
| 2020/0054921 A1* | 2/2020 | Costella ............ A61M 16/0006 |

* cited by examiner

MODULAR EXHALATION DEVICE THAT TRANSITIONS CIRCUITS BETWEEN ACTIVE AND NON-INVASIVE VENTILATION MODES

CROSS-REFERENCE TO RELATED APPLICATIONS

This patent application claims the priority benefit under 35 U.S.C. § 119(e) of U.S. Provisional Application No. 62/771,646, filed on Nov. 27, 2018, the contents of which are herein incorporated by reference.

1. FIELD OF THE INVENTION

The present disclosure is directed generally to systems for an exhalation device that quickly converts between active and passive ventilation.

2. BACKGROUND

Non-invasive ventilation (NIV) uses an active or passive ventilation system to provide gases to a patient using a non-invasive connection between the device and the patient's airway, such as a mask over the patient's mouth and nose, a nasal cannula, or a tracheostomy tube, among other options. Invasive ventilation provides gases to a patient using an invasive connection between the device and the patient's airway such as an endotracheal tube and other connections.

The exhalation circuit for non-invasive ventilation comes in several different types, including passive and active. These exhalation circuits typically comprise an exhalation device which is specifically configured for either passive ventilation or active ventilation. An exhalation device for passive ventilation, for example, is a component that has a leak path which provides a constant path to atmosphere and bleeds off $CO_2$ continuously.

A single limb active exhalation circuit is constructed with an exhalation device, which includes the ability to only open to atmosphere during patient exhalation, and to close the air path from the ventilator to patient during patient inspiration. The ventilator controls an active exhalation valve, opening to atmosphere, with a pressure line. Accordingly, the exhalation device for single-limb active ventilation is able to act similar to a dual-limb circuit by activating a valve which closes the path to atmosphere during the inspiration phase of a patient breath.

However, the exhalation circuit for single-limb non-invasive ventilation is provided with an exhalation device designed for either passive ventilation or active ventilation. There are no exhalation circuits or exhalation devices that are quickly and easily converted back and forth between active and passive ventilation.

SUMMARY OF THE INVENTION

There is a need for non-invasive ventilation exhalation devices that can be converted between active and passive ventilation. Various embodiments and implementations herein are directed to an exhalation device for a non-invasive ventilator system. During passive ventilation, the exhalation device has a constant passive leak to clear $CO_2$, similar to existing non-invasive exhalation ports. During active ventilation, an adapter is added to the exhalation device to transform the passive exhalation device to an active exhalation device. Once the adapter is installed, the ventilator will close or open an exhalation valve with an additional pressure line, thereby converting the passive exhalation circuit into an active exhalation circuit. To convert the active exhalation circuit back to a passive exhalation circuit, the adapter is removed from the exhalation device.

Generally, in one aspect, an exhalation device for a non-invasive ventilator system is provided. The exhalation device is configured to reversibly convert between a first, passive ventilation configuration and a second, active ventilation configuration. The exhalation device includes: (i) a housing with a first end and a second end, the housing defining a gas flow path extending between the first end and the second end; (ii) an exhalation port defined within the housing along the airway path, the exhalation port configured to passively release gas from the gas flow path to the environment; (iii) an internal diaphragm positioned at an interface between the exhalation port and the housing, the internal diaphragm configured to allow release of gas to the exhalation port during exhalation and (iv) an adapter comprising an adapter exhalation port and configured to reversibly engage the exhalation port to define a controlled exhalation flow path from the exhalation port to the adapter exhalation port, the adapter comprising an internal air flow control configured to actively control the flow of exhalant through the controlled exhalation flow path, where the internal diaphragm is configured to be moved out of the airway path by the adapter exhalation port when the adapter engages the exhalation port; and where the exhalation device is in the first, passive ventilation configuration when the adapter is removed from the exhalation port, and further wherein the exhalation device is in the second, active ventilation configuration when the adapter engages the exhalation port.

According to an embodiment, the adapter includes a pressure port configured to enable control of the internal air flow control.

According to an embodiment, the housing includes a proximal pressure port.

According to an embodiment, the exhalation port is configured to engage a filter or a filtering device.

According to an embodiment, the internal air flow control of the adaptor comprises a valve, a diaphragm, or a plateau exhalation valve.

According to an embodiment, the exhalation device is configured for a single-limb patient breathing circuit.

According to an embodiment, the adapter includes an engagement portion configured to reversibly engage the exhalation port.

According to an embodiment, the engagement portion of the adapter comprises a snap fit configured to engage the exhalation port. According to an embodiment, the engagement portion of the adapter is threaded to reversibly engage the exhalation port using complementary threading.

According to an embodiment, the internal diaphragm is configured to move back into the airway path when the adapter disengages the exhalation port. According to an embodiment, the internal diaphragm is configured to provide a predetermined leak profile when the device is in the passive ventilation configuration.

According to another aspect is an exhalation device system for a non-invasive ventilator system configured to reversibly convert between a first, passive ventilation configuration and a second, active ventilation configuration. The exhalation device system includes: an exhalation device comprising: (i) a housing with a first end and a second end, the housing defining a gas flow path extending between the first end and the second end; and (ii) an exhalation port defined within the housing along the airway path, the exhalation port configured to passively release gas from the gas flow path to the environment; and (iii) an internal diaphragm positioned at an interface between the exhalation port and the housing, the internal diaphragm configured to allow release of gas to the exhalation port during exhalation; an adapter comprising an adapter exhalation port and configured to reversibly engage the exhalation port to define a controlled exhalation flow path from the exhalation port to the adapter exhalation port, the adapter comprising an internal air flow control configured to actively control the flow of exhalant through the controlled exhalation flow path, where the internal diaphragm is configured to be reversibly moved out of the airway path by the adapter exhalation port when the adapter engages the exhalation port; and where the exhalation device system comprises a first, passive ventilation configuration when the adapter is removed from the exhalation port, and further wherein the exhalation device system comprises a second, active ventilation configuration when the adapter engages the exhalation port to define the controlled exhalation flow path.

As used herein for purposes of the present disclosure, the term "controller" is used generally to describe various apparatus relating to the operation of a ventilator apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a ventilator system with a configurable exhalation device. More generally, Applicant has recognized and appreciated that it would be beneficial to provide a non-invasive ventilation system with an exhalation device which can be converted back and forth between active and passive ventilation. During passive ventilation, the exhalation device has a constant passive leak to clear $CO_2$. During active ventilation, an adapter is added to the exhalation device to transform the passive exhalation device to an active exhalation device. Once the adapter is installed, the ventilator will close or open an exhalation valve or diaphragm with an additional pressure line, or use a plateau exhalation valve, thereby converting the passive exhalation circuit into an active exhalation circuit. To convert the active exhalation circuit back to a passive exhalation circuit, the adapter is removed from the exhalation device.

The exhalation device design disclosed and described herein can be used with any non-invasive ventilation system designed for or otherwise capable of both passive and active ventilation. Examples of non-invasive ventilation systems that the exhalation device can be used with include, but are not limited to, the Respironics V60 non-invasive ventilator and the Respironics Trilogy ventilator available from Koninklijke Philips N.V.

Figure 1:
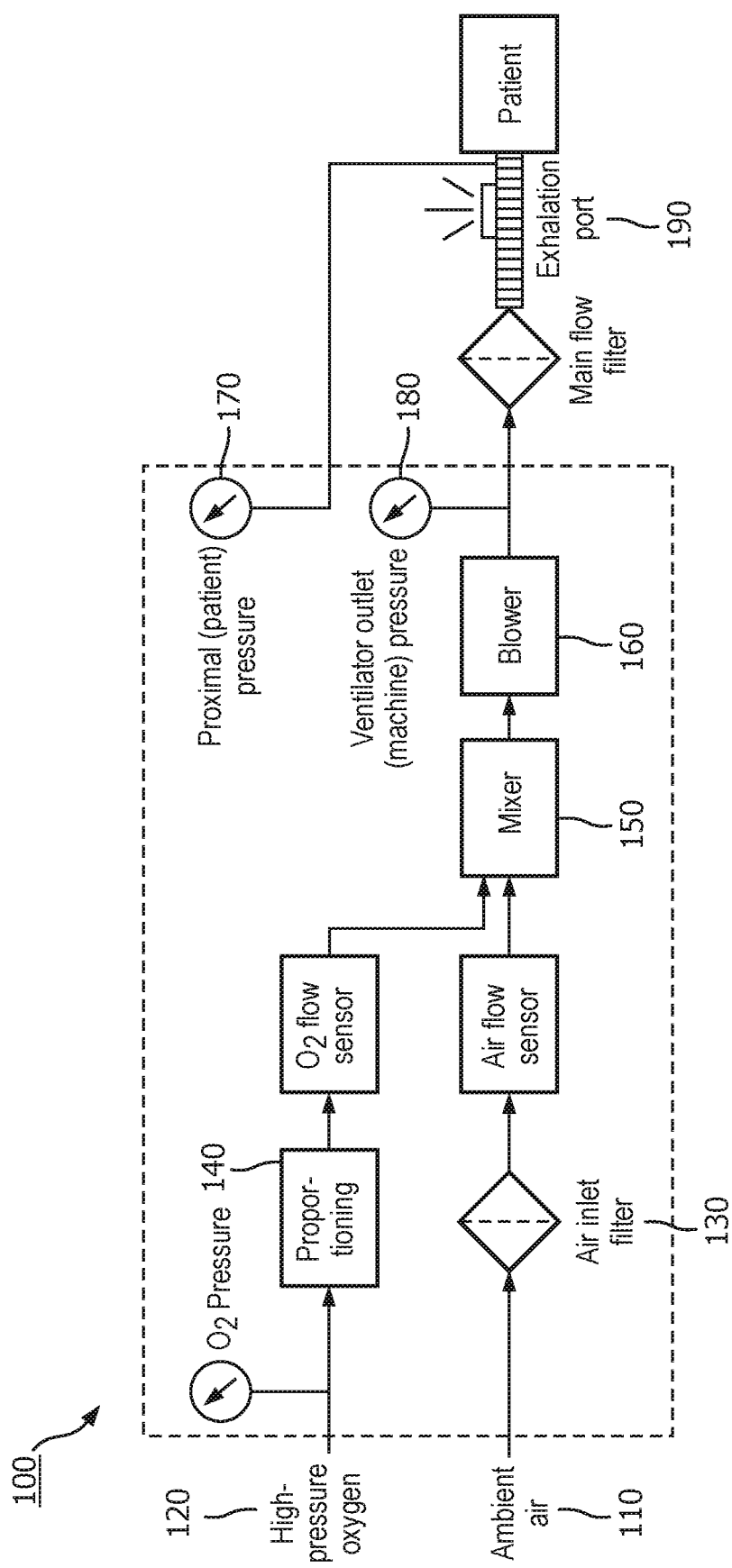
FIG. 1 is a schematic representation of a non-invasive ventilator system, in accordance with an embodiment.

Referring to FIG. 1, in one embodiment, is a diagrammatic representation of an example non-invasive ventilation system 100. In this embodiment, the system is a single limb ventilator with a leak flow near the patient connection, and such that patient-exhaled gas has the potential to travel in a reverse direction through the blower during exhalation. The ventilator uses ambient air 110 and high-pressure oxygen 120. Air enters through an inlet filter 130 and oxygen enters through a high-pressure inlet, where a proportioning valve 140 provides the operator-set concentration. The system mixes the air and oxygen in mixer 150, pressurizes it in the blower 160, and then regulates it to the user-set pressure. To ensure the user-set pressure and compensate for leaks, the ventilator can compare the proximal (patient) pressure measurement obtained by sensor 170 with the ventilator outlet (machine) pressure obtained by sensor 180, and can adjust the machine pressure to compensate for the pressure drop across the patient circuit. The ventilator delivers gas to the patient through a single-limb patient breathing circuit and a patient interface such as a mask or ET tube. During passive exhalation, an exhalation port 190 continually exhausts gas from the circuit during inspiration and exhalation to minimize rebreathing and ensure $CO_2$ removal.

Figure 2:
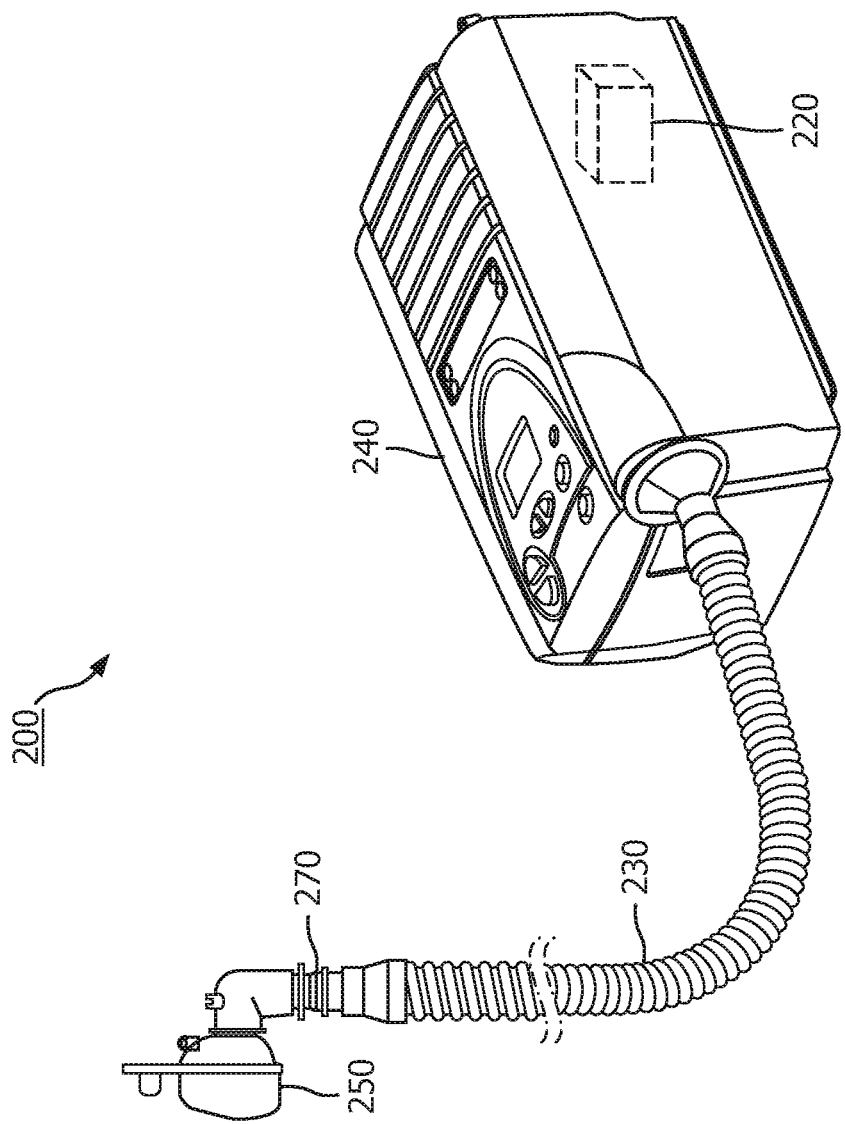
FIG. 2 is a schematic representation of a non-invasive ventilator system, in accordance with an embodiment.

Referring to FIG. 2, in one embodiment, is another representation of an example non-invasive ventilation system 200. The system includes a controller 220, which can be a conventional microprocessor, an application specific integrated circuit (ASIC), a system on chip (SOC), and/or a field-programmable gate arrays (FPGA), among other types of controllers. The controller 220 can be coupled with or otherwise in communication with any needed memory, power supply, I/O devices, control circuitry, and/or other devices necessary for operation of the system.

According to an embodiment, non-invasive ventilation system 200 includes a tube or tubing 230 that delivers gas from the remote ventilator component 240 to the patient interface 250. Patient interface 250 can be, for example, a face mask that covers all or a portion of the patient's mouth and/or nose. There may be masks of many different sizes to accommodate patients or individuals of different sizes, and/ or the mask may be adjustable. As another alternative, patient interface 250 may fit within or on, or otherwise interact with, a tracheostomy tube. Accordingly, the patient interface 250 may be a variety of sizes to accommodate tracheostomies of different shapes and sizes. The patient interface is configured to fit with at least a portion of the patient's airway. The patient end of tubing 230 also includes a traditional exhalation device 270 with a constant passive leak to clear $CO_2$ during passive exhalation.

According to an embodiment, system 200 uses both ambient air and a high-pressure gas source, such as an oxygen source, to produce the gas delivered to the patient. The gas source can be any gas source that might be utilized, such as surrounding environmental air, an oxygen tank, a nitrogen tank, mixtures thereof, as well as a very wide variety of other gas sources.

According to an embodiment, the non-invasive ventilation system also includes a user interface (UI). UI includes graphical, textual and/or auditory information that the system presents to the user, such as a clinician, as well as the control sequences—such as keystrokes, computer mouse movements or selections, and/or touchscreen movements or selections, among other control sequences—that the user utilizes to control the system. In one embodiment, the UI is a graphical user interface such as a display screen. The display screen may include, for example, a touchscreen enabling the user to change one or more settings of the non-invasive ventilation system, as well as a graphical output that displays breathing and ventilation information to the user. For example, the user interface may include an interface such as a button or switch that the user pushes, slides, switches, or otherwise activates in order to switch the device from a passive mode to an active mode pursuant to the embodiments described or envisioned herein.

Figure 3:
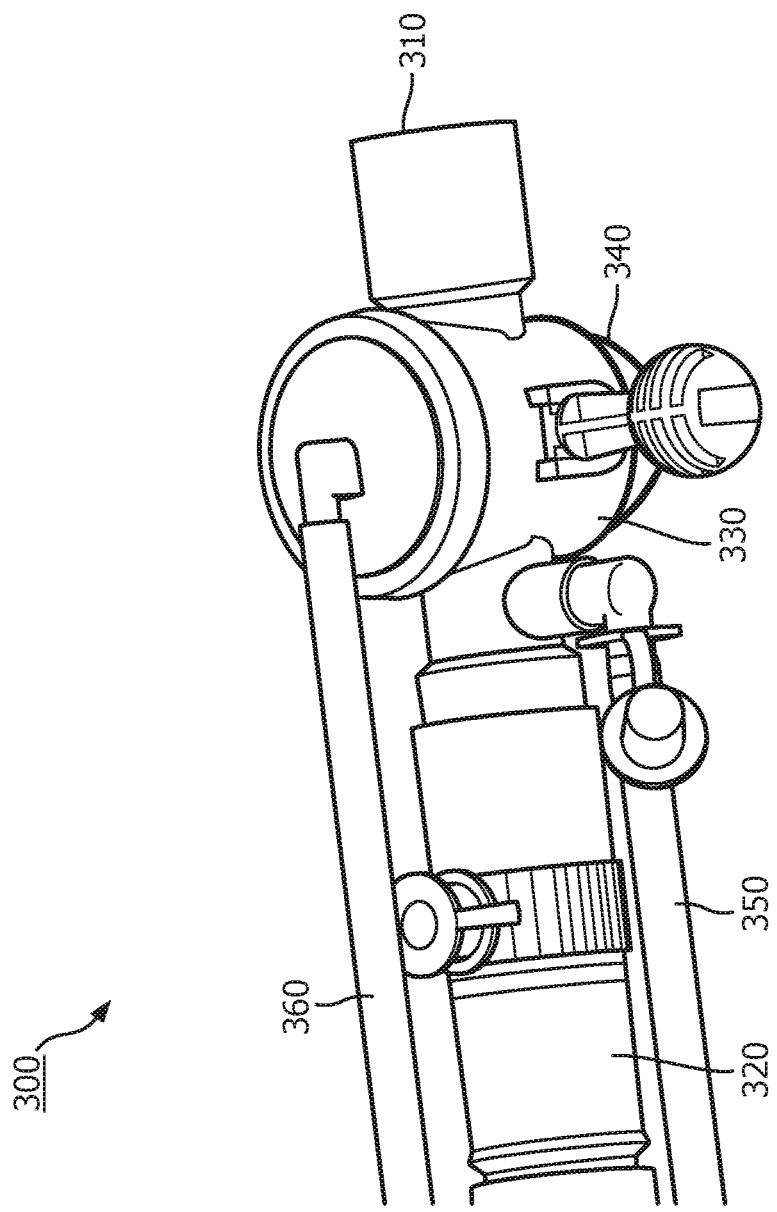
FIG. 3 is a schematic representation of a prior art active exhalation device.

Referring to FIG. 3 is a prior art embodiment of an active circuit for a non-invasive ventilator system. The exhalation device 300 includes a patient end 310, a ventilator end 320, an active exhalation component 330 with an exhalation port 340, proximal pressure tubing 350, and exhalation tubing 360. Patient end 310 is configured to comprise or engage or otherwise communicate with tubing or other connector to lead to a patient interface, and ventilator end 320 is configured to comprise or engage or otherwise communicate with tubing or other connector to lead to a ventilator. Proximal pressure tubing 350 is configured to enable a proximal pressure sensor to obtain proximal pressure measurements.

During ventilation, active exhalation component 330 is controlled to allow the passage of air from the ventilator end 320 to the patient end 310 during inhalation, and to allow the passage of from the patient end 310 to the exhalation port 340 during exhalation. The flow of air is optionally controlled by a valve (not shown) internal to the active exhalation component 330. According to one embodiment, during inhalation a pressure applied to the valve via the exhalation tubing 360 keeps the valve in a position that prevents air to be drawn into the system via the exhalation port 340. During exhalation, that pressure is either lessened or not applied and the valve moves to a position that allows air to be exhaled via the exhalation port 340.

Figure 4:
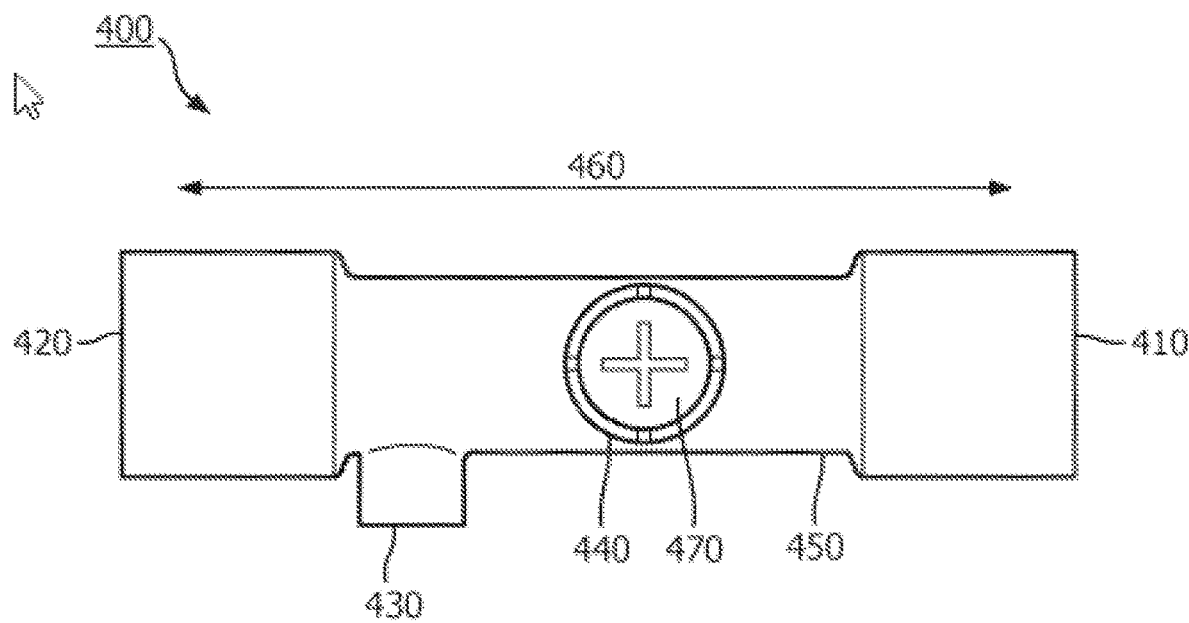
FIG. 4 is a schematic representation of an exhalation device in a passive configuration, in accordance with an embodiment.

Referring to FIG. 4, in one embodiment, is a configurable exhalation device 400 in a passive ventilation configuration, which will be located proximal to the patient, between the patient and the ventilator such as the location shown in FIGS. 2 and 3. The exhalation device 400 includes a patient end 410 leading toward a patient (not shown) and a ventilator end 420 leading to the ventilator (not shown). For example, the patient end 410 may interface or comprise tubing that leads to a patient interface. The ventilator end 420 may interface or comprise tubing that leads to the ventilator. The exhalation device 400 includes a hollow housing 450 that defines a gas flow path (represented by dotted arrow 460) between patient end 410 and ventilator end 420, such that air can flow in one direction and/or the other, from one end to the other.

Exhalation device 400 includes an optional port 430 which can be used to measure or obtain pressure to measure the proximal pressure. For example, port 430 may be connected to or otherwise in communication with proximal pressure tubing leading to the ventilator and/or a proximal pressure sensor.

Exhalation device 400 also includes an exhalation port 440 that exhausts gas from the circuit during inspiration and exhalation to minimize rebreathing and ensure $CO_2$ removal. As shown by comparing FIGS. 4 and 5, exhalation port 440 extends outwardly from the housing 450 of the device, although 400 is not necessarily to scale in these images, and the length of 440 can vary depending on the design and/or utilization of the exhalation device. At the interface of the exhalation port and the hollow housing 450 is a diaphragm 470. Diaphragm 470 is selected or designed to provide a particular leak profile to the exhalation device when the device is in the passive configuration. Diaphragm 470 is configured to be flexible such that when the adapter 600 is connected to the exhalation port 440, a portion of the adapter pushes against at least a portion of the diaphragm, pushing the diaphragm out of the way to open the airway between the hollow housing 450 and the exhalation device engagement portion 610 of adapter 600. However, the diaphragm is positioned within the device such that when it is displaced, it does not block the airway within either the housing 450 or the adapter 600. Accordingly, diaphragm 470 is composed of a material, such as a flexible plastic, that provides the desired leak profile in the passive configuration, flexes out of the airway path when the adapter 600 is connected to the exhalation device in the active configuration, and flexes back into the airway path again with the desired leak profile when the adapter 600 is removed from the exhalation device.

Figure 5:
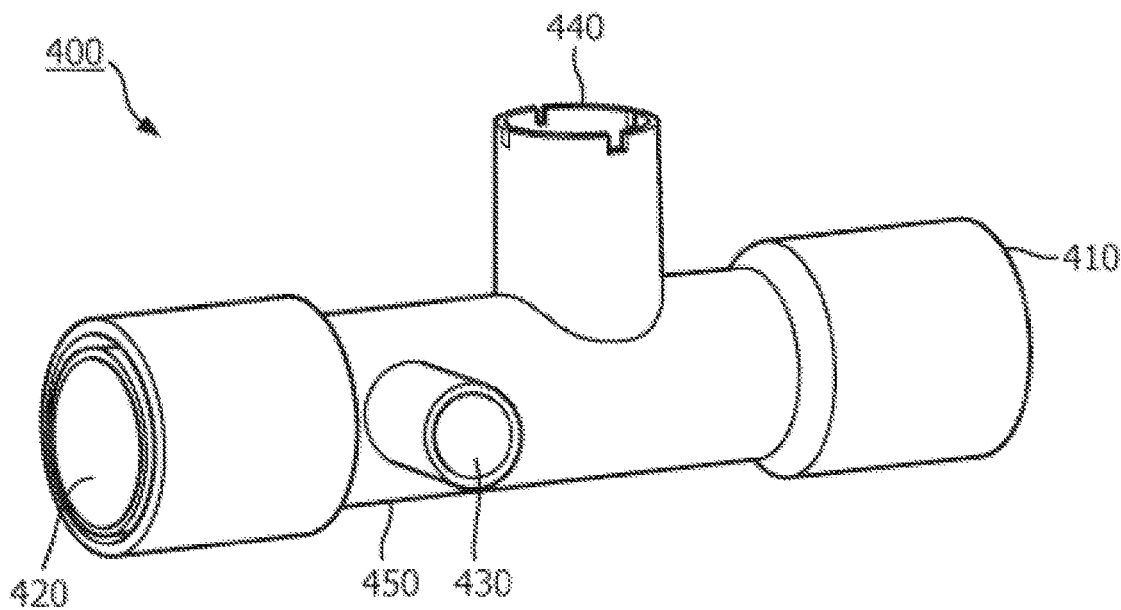
FIG. 5 is a schematic representation of an exhalation device in a passive configuration, in accordance with an embodiment.

Referring to FIG. 5, in one embodiment, is the configurable exhalation device 400 rotated to show a different angle. The exhalation device 400 is in a passive ventilation configuration, and comprises a housing 450 with a patient end 410 and a ventilator end 420, optional port 430, and exhalation port 440.

According to an embodiment, the exhalation port 440 is configured to engage a filter or a component comprising a filter, thus enableing filtration of exhalation. The filter may be any filter now used or used in the future for filtering within a ventilation system. Filtering exhaust flow protects caregivers, and everyone else, if a patient has an airborne illness, among other possible benefits.

Although it is internal and not shown in FIG. 5, the opening between the housing 450 and the exhalation port 440 comprises the diaphragm 470 which provides a necessary leak profile but enables an open airway path from the housing through the port to the exhalation device engagement portion 610 when the adapter 600 is connected to the exhalation port.

Figure 6:
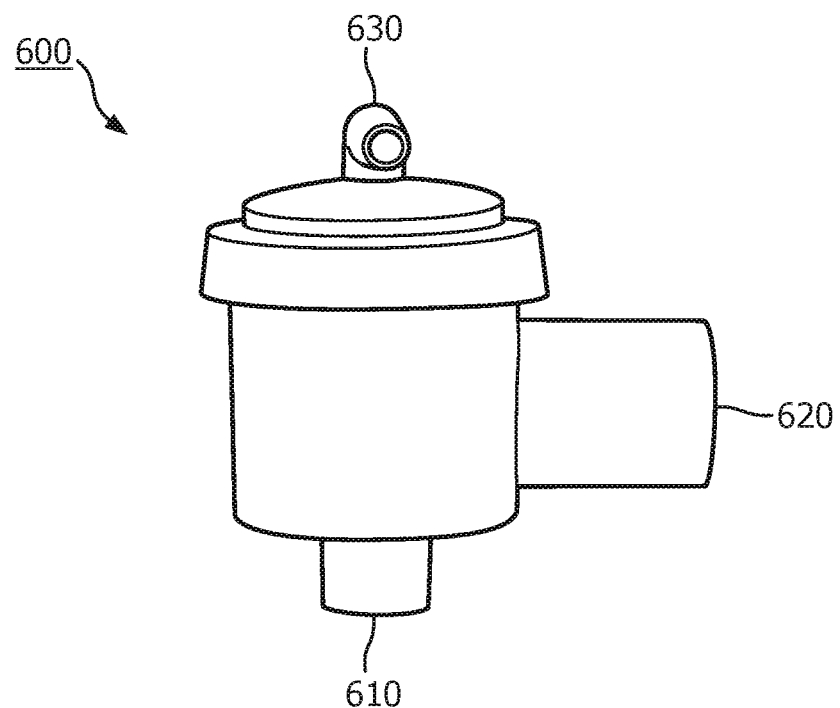
FIG. 6 is a schematic representation of an exhalation device adapter, in accordance with an embodiment.

Referring to FIG. 6, in one embodiment, is an adapter 600 configured to convert the exhalation device from a first, passive configuration to a second, active configuration. Adapter 600 may take many forms, and only one configuration or form of the adapter is shown in FIG. 6. According to an embodiment, adapter 600 comprises an exhalation device engagement portion 610, an exhalation port 620, and a pressure port 630. The pressure port 630 is configured to engage, connect to, or otherwise communicate with exhalation tubing (not shown) that leads back to the ventilator or other ventilation control component. The exhalation port 620 is configured to allow exhalation of air during exhalation.

According to one embodiment, adapter 600 includes air flow control mechanism, such as an internal valve or diaphragm, configured to control the flow of air during active ventilation. The air flow control mechanism of adapter 600 may be in communication with, and controlled by, pressurized air delivered via pressure port 630 from the ventilator. For example, during inhalation a pressure applied to the valve via pressurized air delivered via pressure port 630, including optionally via exhalation tubing connected to pressure port 630, keeps the valve in a position that prevents air to be drawn into the system via the device engagement portion 610 and the exhalation port 620, thus forcing air to be drawn into the system via ventilator end 420 leading from the ventilator. During exhalation, that pressure is either lessened or not applied and the valve moves to a position that allows air to be exhaled via the exhalation port 620. According to the configuration of the air flow control mechanism, the valve or diaphragm may be controlled opposite to the method described here, with applied air pressure allowing air to be exhaled via the exhalation port 620. According to another embodiment, the air flow control mechanism of the adapter 600 is a component such as a plateau exhalation valve (PEV) or a similarly operated mechanism to minimize rebreathing.

The adapter 600 may be connected to the exhalation port 440 of the configurable exhalation device 400 using any method or mechanism of attachment suitable to prevent significant leak. For example, the adapter and/or exhalation port may be sized or otherwise configured such that the adapter is positioned within the exhalation port using a tapered locking fit, via screwing or a twist lock with or without threads (in which case the adapter 600 and exhalation port 440 may comprise complementary threads), a snap fit, or any other method or mechanism.

According to an embodiment, the exhalation device engagement portion 610 of adapter 600 engages diaphragm 470 of the exhalation device 400 to push the diaphragm out of the path of exhaled air, such that there is no resistance between the hollow housing 450 and the airway within the engagement portion 610. The resistance is then provided by the air flow control mechanism of the adapter 600 rather than the diaphragm. When the adapter 600 is removed from the exhalation device 400, the diaphragm will self-heal, or return to the normal position, and again provide the necessary leak profile.

According to an embodiment, adapter 600 may comprise or be configured to engage a filter or a component comprising a filter (not shown). The filter may be any filter, including any material, known to be used now or in the future for air filtration.

Figure 7:
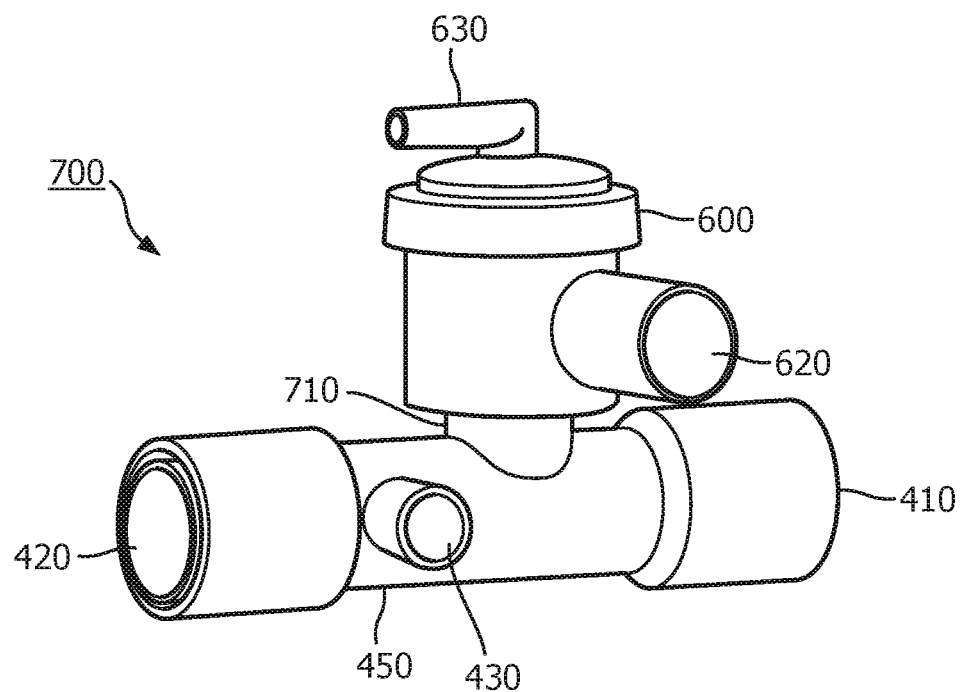
FIG. 7 is a schematic representation of an exhalation device in an active configuration, in accordance with an embodiment.

Referring to FIG. 7, in one embodiment, is an assembled exhalation device 700 in an active ventilation configuration with the exhalation device 400 and the adapter 600 assembled or connected. With the adapter 600 installed, the ventilator will close or open the exhalation valve with the additional pressure line, thereby converting the passive exhalation circuit into an active exhalation circuit.

The assembled exhalation device 700 comprises a hollow housing 450 that defines a gas flow path between a patient end 410 leading toward a patient (not shown) and a ventilator end 420 leading to the ventilator (not shown). The assembled exhalation device 700 further comprises an optional port 430 which can be used to measure or obtain pressure to measure the proximal pressure. For example, port 430 may be connected to or otherwise in communication with proximal pressure tubing leading to the ventilator and/or a proximal pressure sensor. The assembled exhalation device 700 also includes an exhalation port 620 and a pressure port 630. Since exhalation device 700 is assembled, exhalation port 440 and device engagement portion 610 are interacting, engaged, or otherwise connected at interface 710 and thus are not individually shown.

To complete the active configuration, the ventilator mode is changed along with the addition of adaptor 600. During inhalation a pressure applied to the internal valve of the adapter 600 via pressurized air delivered via pressure port 630, including optionally via exhalation tubing connected to pressure port 630, keeps the internal valve in a position that prevents air to be drawn into the system via the device engagement portion 610 and the exhalation port 620, thus forcing air to be drawn into the system via ventilator end 420 leading from the ventilator. During exhalation, that pressure is either lessened or not applied and the valve moves to a position that allows air to be exhaled via the exhalation port 620.

Assembly is reversible, and thus the assembled exhalation device 700 of FIG. 7, which is in the active configuration, may be converted or reverted to the exhalation device 400 of FIG. 4, which is in the passive configuration. Conversion comprises removal of the adapter 600, which requires reversal or manipulation of the connection method or mechanism. For example, the adapter may be unscrewed from, pulled out of, unsnapped from, or otherwise removed or disconnected from the exhalation device. Once the adapter is removed, the exhalation device is in the passive configuration.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. An exhalation device for a non-invasive ventilator system, the exhalation device configured to reversibly convert between a first, passive ventilation configuration and a second, active ventilation configuration, the exhalation device comprising:
   a housing with a first end and a second end, the housing defining a gas flow path extending between the first end and the second end, wherein the first end and the second end are both open ends;
   an exhalation port defined within the housing, the exhalation port configured to passively release gas from the gas flow path to the environment;
   an internal diaphragm positioned at an interface between the exhalation port and the housing, the internal diaphragm configured to allow release of gas to the exhalation port during exhalation; and
   an adapter comprising an adapter exhalation port, and further comprising an engagement portion configured to reversibly engage the exhalation port to define a controlled exhalation flow path from the exhalation port to the adapter exhalation port, the adapter comprising an internal air flow control configured to actively control the flow of exhalant through the controlled exhalation flow path;
   wherein the internal diaphragm is configured to be at least partially moved out of the gas flow path by the adapter when the engagement portion of the adapter engages the exhalation port, wherein the exhalation device is in the first, passive ventilation configuration when the adapter is removed from the exhalation port, and further wherein the exhalation device is in the second, active ventilation configuration when the engagement portion of the adapter engages the exhalation port.

2. The exhalation device of claim 1, wherein the adapter further comprises a pressure port configured to enable control of the internal air flow control.

3. The exhalation device of claim 1, wherein the housing comprises a proximal pressure port.

4. The exhalation device of claim 1, wherein the adaptor comprises a filter or filter device.

5. The exhalation device of claim 1, wherein the internal air flow control of the adaptor comprises a valve, diaphragm, or plateau exhalation valve.

6. The exhalation device of claim 1, wherein the exhalation device is configured for a single-limb patient breathing circuit.

7. The exhalation device of claim 1, wherein the engagement portion is further configured to reversibly engage the exhalation port.

8. The exhalation device of claim 7, wherein the engagement portion of the adapter comprises a snap fit configured to engage the exhalation port.

9. The exhalation device of claim 7, wherein the engagement portion of the adapter is threaded to reversibly engage the exhalation port using complementary threading.

10. The exhalation device of claim 1, wherein the internal diaphragm is configured to move back into the airway path when the adapter disengages the exhalation port.

11. The exhalation device of claim 1, wherein the internal diaphragm is configured to provide a predetermined leak profile when the device is in the passive ventilation configuration.

12. An exhalation device system for a non-invasive ventilator system, the exhalation device system configured to reversibly convert between a first, passive ventilation configuration and a second, active ventilation configuration, the exhalation device system comprising:
an exhalation device comprising: (i) a housing with a first end and a second end, the housing defining a gas flow path extending between the first end and the second end, wherein the first end and the second end are both open ends; (ii) an exhalation port defined within the housing, the exhalation port configured to passively release gas from the gas flow path to the environment; and (iii) an internal diaphragm positioned at an interface between the exhalation port and the housing, the internal diaphragm configured to allow release of gas to the exhalation port during exhalation; and
an adapter comprising an adapter exhalation port, and further comprising an engagement portion configured to reversibly engage the exhalation port to define a controlled exhalation flow path from the exhalation port to the adapter exhalation port, the adapter comprising an internal air flow control configured to actively control the flow of exhalant through the controlled exhalation flow path;
wherein the internal diaphragm is configured to be at least partially reversibly moved out of the gas flow path by the adapter when the engagement portion of the adapter engages the exhalation port, wherein the exhalation device system comprises the first, passive ventilation configuration when the adapter is removed from the exhalation port, and further wherein the exhalation device system comprises the second, active ventilation configuration when the engagement portion of the adapter engages the exhalation port to define the controlled exhalation flow path.

13. The exhalation device system of claim 12, wherein the exhalation device further comprises a proximal pressure port.

14. The exhalation device system of claim 12, wherein the internal air flow control of the adaptor comprises a valve, diaphragm, or plateau exhalation valve.

15. The exhalation device system of claim 12, wherein the engagement portion is further configured to reversibly engage the exhalation port.

16. An exhalation device for a non-invasive ventilator system, the exhalation device configured to reversibly convert between a first, passive ventilation configuration and a second, active ventilation configuration, the exhalation device comprising:
a housing with a first end and a second end, the housing defining a gas flow path extending between the first end and the second end, wherein the first end and the second end are both open ends;
an exhalation port defined within the housing, the exhalation port configured to passively release gas from the gas flow path to the environment;
an internal diaphragm positioned at an interface between the exhalation port and the housing, the internal diaphragm configured to allow release of gas to the exhalation port during exhalation; and
an adapter comprising an adapter exhalation port, and further comprising an engagement portion configured to reversibly engage the exhalation port to define a controlled exhalation flow path from the exhalation port to the adapter exhalation port, the adapter comprising an internal air flow control configured to actively control the flow of exhalant through the controlled exhalation flow path;
wherein the internal diaphragm is configured to be at least partially moved out of the gas flow path by the adapter when the engagement portion of the adapter engages the exhalation port, wherein the exhalation device is in the first, passive ventilation configuration when the adapter is removed from the exhalation port, and further wherein the exhalation device is in the second, active ventilation configuration when the engagement portion of the adapter engages the exhalation port
wherein the engagement portion of the adaptor is further configured to reversibly engage the exhalation port via a snap fit, or wherein the engagement portion of the adapter is threaded to reversibly engage the exhalation port using complementary threading.

* * * * *